United States Patent [19]

Shimamura et al.

[11] Patent Number: 5,205,151

[45] Date of Patent: Apr. 27, 1993

[54] ALCOHOL CONCENTRATION SENSOR TESTING APPARATUS

[75] Inventors: Masahiko Shimamura; Kazumitsu Koboyashi; Hideki Kamioka, all of Gunma, Japan

[73] Assignee: Japan Electronic Control Systems Co., Ltd., Isezaki, Japan

[21] Appl. No.: 703,091

[22] Filed: May 22, 1991

[30] Foreign Application Priority Data

May 22, 1990 [JP] Japan .................................. 2-132029

[51] Int. Cl.$^5$ .......................................... G01D 18/00
[52] U.S. Cl. .................... 73/1 R; 73/61.43; 73/61.61; 73/1 G; 324/601; 324/690; 324/679
[58] Field of Search .................. 73/1 G, 1 R, 61.1 R, 73/61.43, 61.61, 23.21, 23.3, 31.05, 23.31, 118.1; 324/601, 690, 679, 684, 667, 668, 669

[56] References Cited

U.S. PATENT DOCUMENTS

| | | | |
|---|---|---|---|
| 3,256,482 | 6/1966 | Rosso | 324/669 |
| 4,470,300 | 9/1984 | Kobayashi | 324/677 X |
| 4,555,941 | 12/1985 | Fathauer et al. | 73/1 H X |
| 4,624,139 | 11/1986 | Collins | 324/601 X |
| 4,676,100 | 6/1987 | Eichberger | 73/1 H X |
| 4,788,488 | 11/1988 | Kramer et al. | 324/601 X |
| 4,939,468 | 7/1990 | Takeuchi | 324/663 X |
| 5,033,293 | 7/1991 | Honma et al. | 73/118.1 |
| 5,048,335 | 9/1991 | Marsh et al. | 324/601 X |

FOREIGN PATENT DOCUMENTS 3923992 1/1990 Fed. Rep. of Germany .
1526196 9/1978 United Kingdom ................ 324/679

OTHER PUBLICATIONS

*Patent Abstract of Japan* ABS Group No., P1036, vol. 14, No. 185, ABS pub. date Apr. 13, 1990, Abstract of (2–32441) [Japanese family member of German 3932992].

*Primary Examiner*—Tom Noland
*Attorney, Agent, or Firm*—Foley & Lardner

[57] ABSTRACT

An apparatus for testing an alcohol concentration sensor used in measuring an alcohol concentration of a fluid containing alcohol. The alcohol concentration sensor includes a capacitive probe having a capacity dependent upon the alcohol concentration of the fluid, and a circuit sensitive to the capacity of the capacitive probe for producing an output signal indicative of a sensed alcohol concentration. The apparatus comprises a plurality of capacitors having different capacities each corresponding to a predetermined alcohol concentration. A selected one of the capacitors is connected in parallel with the capacitive probe. When the selected capacitor is connected with the capacitive probe, the output signal is read.

10 Claims, 5 Drawing Sheets

| CAPACITIES | ALCOHOL | GASOLINE |
|---|---|---|
| $C_1$ | 0% | 100% |
| $C_2$ | 10% | 90% |
| $C_3$ | 20% | 80% |
| ⋮ | ⋮ | ⋮ |
| $C_0 + C_n$ | 100% | 0% |

ALCOHOL CONCENTRATION SENSOR TESTING APPARATUS

BACKGROUND OF THE INVENTION

This invention relates to an apparatus for testing an alcohol concentration sensor employing capacitive probe to measure an alcohol concentration of a fluid containing alcohol.

For example, alcohol concentration sensors have been used to measure an alcohol concentration of gasoline/alcohol fuel blend supplied to an internal combustion engine operable on either of gasoline fuel and gasoline/alcohol fuel blend. The measured alcohol concentration is used to control the amount of fuel metered to the engine. It is the current practice to test the output characteristic of the alcohol concentration sensor by troublesome operations of exposing the alcohol concentration sensor to gasoline/alcohol fuel blends having different alcohol concentrations. For this reasons, it is impossible to test alcohol concentration sensors with high efficiency.

SUMMARY OF THE INVENTION

Therefore, a main object of the invention to provide an alcohol concentration sensor testing apparatus which can test alcohol concentration sensors with ease and with high efficiency.

There is provided, in accordance with the invention, an apparatus for testing an alcohol concentration sensor used in measuring an alcohol concentration of a fluid containing alcohol. The alcohol concentration sensor includes a capacitive probe having a capacity dependent upon the alcohol concentration of the fluid, and a circuit sensitive to the capacity of the capacitive probe for producing an output signal indicative of a sensed alcohol concentration. The apparatus comprises a plurality of capacitors having different capacities each corresponding to a predetermined alcohol concentration, first means for connecting a selected one of the capacitors in parallel with the capacitive probe, and second means for reading a value of the output signal when the selected capacitor is connected with the capacitive probe.

BRIEF DESCRIPTION OF THE DRAWINGS

The invention will be described in greater detail by reference to the following description taken in connection with the accompanying drawings, in which.

DETAILED DESCRIPTION OF THE INVENTION

Figure 1:
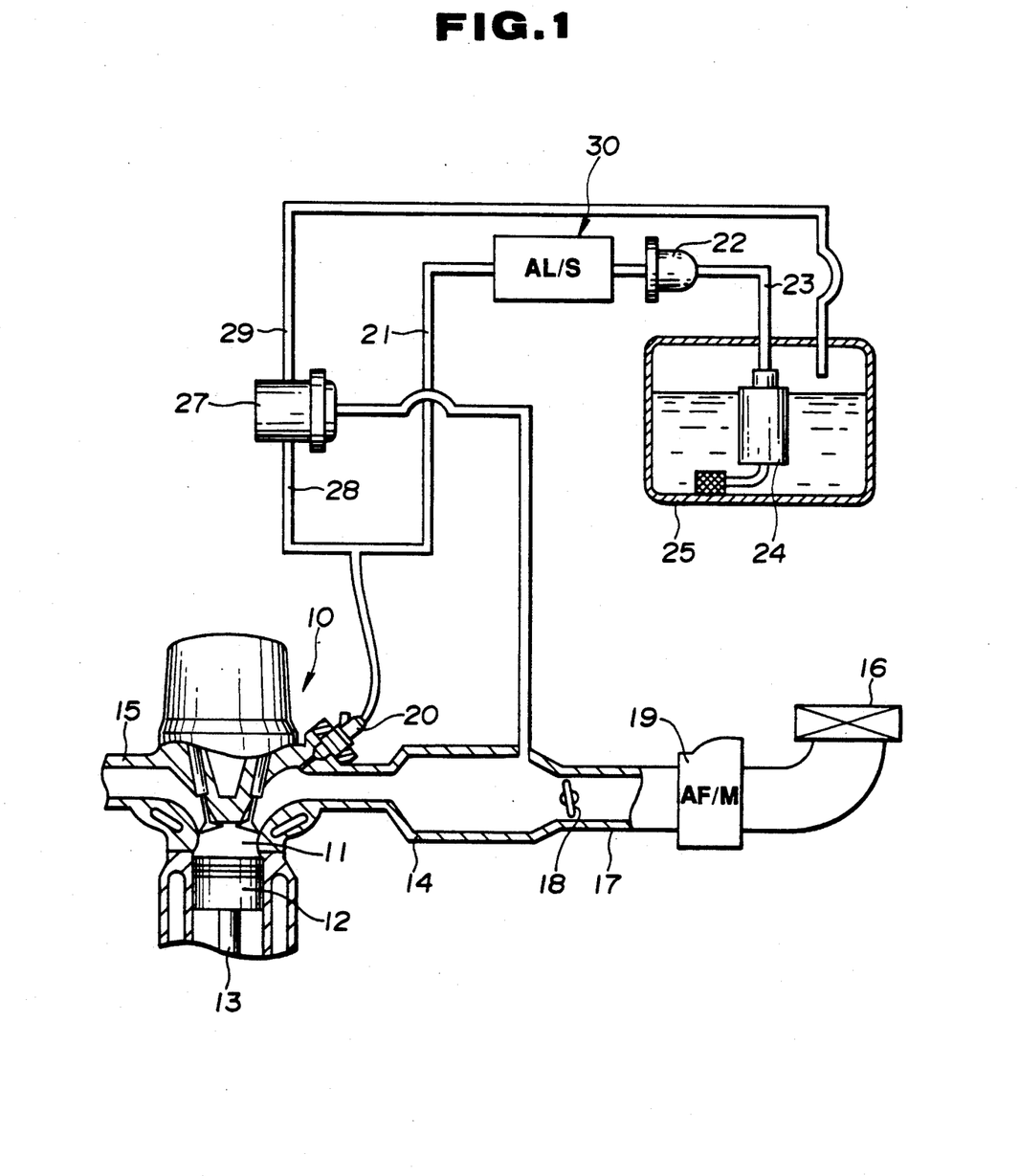
FIG. 1 is a schematic view showing a fuel delivery system used in an internal combustion engine.

With reference to the drawings, wherein like numerals refer to like parts in the several views, and in particular to FIG. 1, there is shown a fuel delivery system for use in conjunction with an internal combustion engine operable on either of gasoline fuel and gasoline/alcohol fuel blend. While the fuel delivery system itself does not form a part of the present invention, it is illustrated to provide a point of reference for this invention in a practical environment.

The internal combustion engine, generally designated by the numeral 10, includes a combustion chamber or cylinder 11. A piston 12 is mounted for reciprocal motion within the cylinder 11. A crankshaft 13 is supported for rotation within the engine 10 in response to reciprocation of the piston 12 within the cylinder 11.

An intake manifold 14 is connected with the cylinder 11 through an intake port with which an intake valve is in cooperation for regulating the entry of combustion ingredients into the cylinder 11 from the intake manifold 14. An exhaust manifold 15 is connected with the cylinder 11 through an exhaust port with which an exhaust valve is in cooperation for regulating the exit of combustion products, exhaust gases, from the cylinder 11 into the exhaust manifold 15.

Air to the engine 10 is supplied through an air cleaner 16 into an induction passage 17. The amount of air permitted to enter the combustion chamber 11 through the intake manifold 14 is controlled by a butterfly throttle valve 18 located within the induction passage 17. A flow meter 19 is located to sense the air flow through the induction passage 17 and it produces an intake airflow signal proportional to the amount of air to the engine. The intake airflow signal is applied to an engine control unit (not shown).

A fuel injector 20 is mounted for injecting fuel into the intake manifold 15 toward the intake valve. The fuel injector 20 is connected by a conduit 21 to a fuel filter 22 which is connected by a conduit 23 to a fuel pump 24 placed in a fuel tank 25. The fuel pump 24 is electrically operated to maintain sufficient pressure. The fuel tank 25 contains a gasoline fuel or a gasoline-alcohol fuel blend. The alcohol fuel may include methanol, ethanol, or methanol/ethanol blend. A fuel pressure regulator 27 is connected by a conduit 28 to the conduit 21 and by a conduit 29 to the fuel tank 25. Preferably, the pressure regulator 27 senses the pressure in the conduit 21 and the pressure within the intake manifold 14 to maintain the differential between these pressures, that is, the pressure differential across the fuel injector 20 at a constant level. This regulation is accomplished by a variation in the amount of excess fuel returned through the return conduit 29 to the fuel tank 25. An alcohol concentration sensor 30 is located in the conduit 21 to sense an alcohol concentration contained in the fuel delivered to the fuel injector 20 and it produces an alcohol concentration signal indicative of a sensed alcohol concentration. The alcohol concentration signal is applied to the engine control unit.

The fuel injector 20 opens to inject fuel into the intake manifold 15 when it is energized by the presence of an electrical signal. The length of the electrical pulse, that is, the pulse-width, applied to the fuel injector 20 determines the length of time the fuel injector opens and, thus, determines the amount of fuel injected into the intake manifold 15. The fuel injected through the fuel injector 20 into the intake manifold 14 mixes with the air therein. The air-fuel mixture enters the combustion chamber 11 when the intake valve opens, combustion of the air-fuel mixture takes place in the combustion chamber 11. When the exhaust valve opens, the exhaust gases are discharged into the exhaust manifold 15. The exhaust gases are discharged to the atmosphere through a conventional exhaust system. An oxygen sensor (not shown) is located in the exhaust system to monitor the oxygen content of the exhaust and it is effective to provide an air/fuel ratio signal indicative of the air/fuel ratio at which the engine 10 is operating. The air/fuel ratio signal is applied to the engine control unit.

In the engine control unit, the amount of fuel metered to the engine, this being determined by the width of the electrical pulses applied to the fuel injector 20 is repetitively determined from calculations performed by a digital computer, these calculations being based upon various conditions of the engine that are sensed during its operation. These sensed conditions include cylinder-head coolant temperature, exhaust oxygen content, throttle valve position, engine speed, intake air flow, engine intake-manifold absolute-pressure, and alcohol concentration.

The engine control unit employs a digital computer for calculating the fuel delivery requirement in the form of fuel-injection pulse-width. For this purpose, a basic value Tp for fuel-injection pulse-width is calculated as $$Tp = k \times Q/N$$

where k is a constant, Q is the intake air flow and N is the engine speed. The calculated fuel-injection pulse-width basic value Tp is then corrected for various engine operating parameters. The corrected fuel-injection pulse-width value Ti is given as $$Ti = Tp \times COEF \times ALPHA \times ALK \times KBLRC + Ts$$

where ALPHA is a correction factor related to the oxygen content of the exhaust gases for providing a closed loop air/fuel ratio control, ALC is a correction factor related to the alcohol concentration contained in the fuel delivered to the fuel injector 40, and Ts is a correction factor related to the voltage of the car battery. The air/fuel ratio signal is sampled once for each of sampling events for calculating an average value representing the existing air/fuel ratio. A difference $\Delta ALPHA$ of the calculated average value relative to the stoichiometric value is calculated and stored. During steady engine operating conditions, the engine control unit has a learning control function of relating the calculated difference $\Delta ALPHA$ to existing engine operating conditions, for example, engine load and engine speed. The stored difference $\Delta ALPHA$ is utilized to calculate the correction factor KBLRC which is used to further adjust the calculated injection interval in a direction to correct the sensed air/fuel ratio error. The correction factor COEF is given as $$COEF = 1 + (KMR + KTRM) + KTW + KAS + KAI + KACC$$

where KMR is a correction factor for providing fuel enrichment control under high engine load conditions. The correction factor KMR is greater at a hevier engine load or at a higher engine speed. KTRM is a correction factor for providing fuel leaning control under light engine load conditions. KTW is a correction factor decreasing as the engine coolant temperature increases, KAS is a correction factor for providing fuel enrichment control when the engine is cranking, KAI is a correction factor for providing a fuel enrichment control when the engine is idling, and KACC is a correction factor set at a negative value when the throttle position exceeds a predetermined angle and then it increases toward zero as the engine speed increases.

Figure 2:
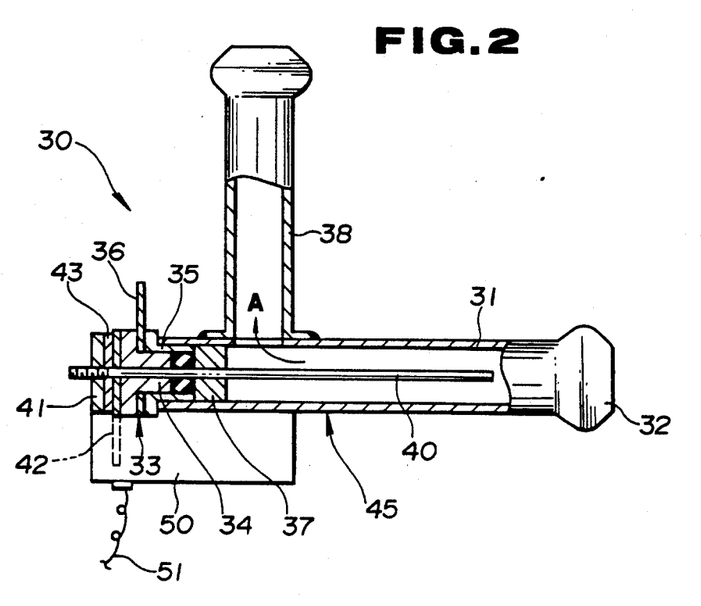
FIG. 2 is a sectional view of an alcohol concentration sensor used in the fuel delivery system of FIG. 1.

Referring to FIG. 2, the alcohol concentration sensor 30 comprises a tube member 31 made of a conducting material. For example, the tube member 31 may be a steel tube plated with nickel. The tube member 31 is provided at its front end with an inlet end 32 for introduction of fuel from the fuel filter 22 and is closed at its rear end with an end fitting 33. The end fitting 33 includes an insulating member 34 and a conducting member 35 fitted tightly into the tube member 31. A terminal member 36 is sandwiched between the insulating and conducting members 34 and 35. The conducting member 35 establishes an electrical connection between the tube member 31 and the terminal member 36. A plug 37 is tightly fitted against the inside of the tube member 31 near the end fitting 33. The plug 37 is made of an insulating material. The tube member 31 is also provided adjacent to the plug 37 with an outlet 38 through which fuel is discharged to the fuel injector 20.

A conducting rod member 40 extends axially into the tube member 31 through the end fitting 33 and the plug 37. The rod member 40 is exposed to fuel flow A through the tube member 31 from the inlet end 32 to the outlet 38. The numeral 42 designates a terminal member through which the rod member 40 extends so that an electrical connection is established between the rod member 40 and the terminal member 42. The rod member 40 has a threaded end portion to which a nut 41 is screwed to fasten the terminal member 42 on the rear end surface of the insulating member 34. A washer 43 is disposed between the nut 41 and the terminal member 42. The conducting rod member 40 forms a capacitive probe 45 along with the conducting tube member 31 surrounding the conductive rod member 40. The capacitive probe 45 has a capacitance variable in dependence on the alcohol concentration of the fuel to which the capacitive probe is exposed. The terminal members 36 and 42 are connected to an alcohol concentration measuring unit 50 which produces the alcohol concentration signal through a line 51 to the engine control unit.

Figure 3:
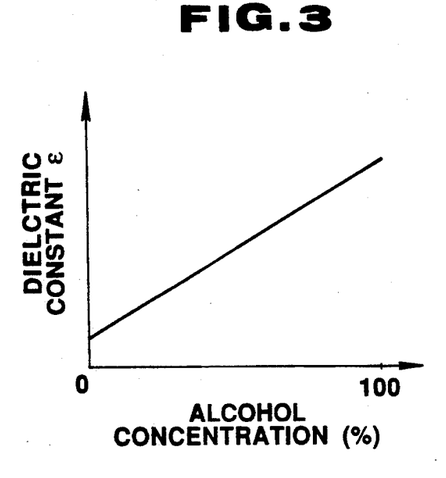
FIG. 3 is a graph of alcohol concentration versus dielectric constant.
Figure 4:
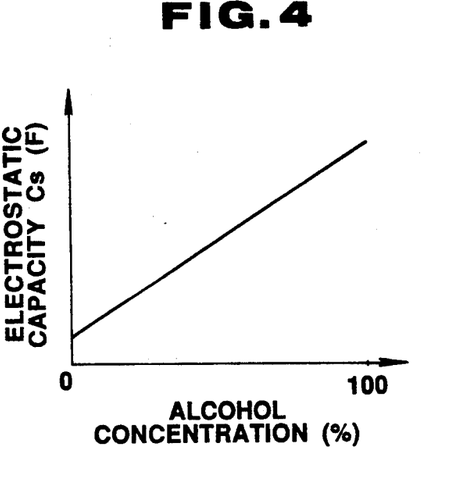
FIG. 4 is a graph of alcohol concentration versus electrostatic capacity.

The capacitive probe 45 has an electrostatic capacity Cs given as $$Cs = \frac{2 \times \pi \times l \times \epsilon}{\cosh^{-1} \frac{R1^2 + R2^2}{2 \times R1 \times R2}}$$

where $\epsilon$ is the dielectric constant of the gasoline/alcohol fuel blend, l is the length of the conducting rod member 40, R1 is the diameter of the conducting rod member 40 and R2 is the diameter of the conducing tube member 31. The dielectric constant of the gasoline/alcohol fuel blend has a linear relationship with the alcohol concentration M of the gasoline/alcohol fuel blend, as shown in FIG. 3 and, thus, the electrostatic capacity Cs of the capacitive probe 45 has a linear relationship with the alcohol concentration M of the gasoline/alcohol fuel blend, as shown in FIG. 4.

Figure 5:
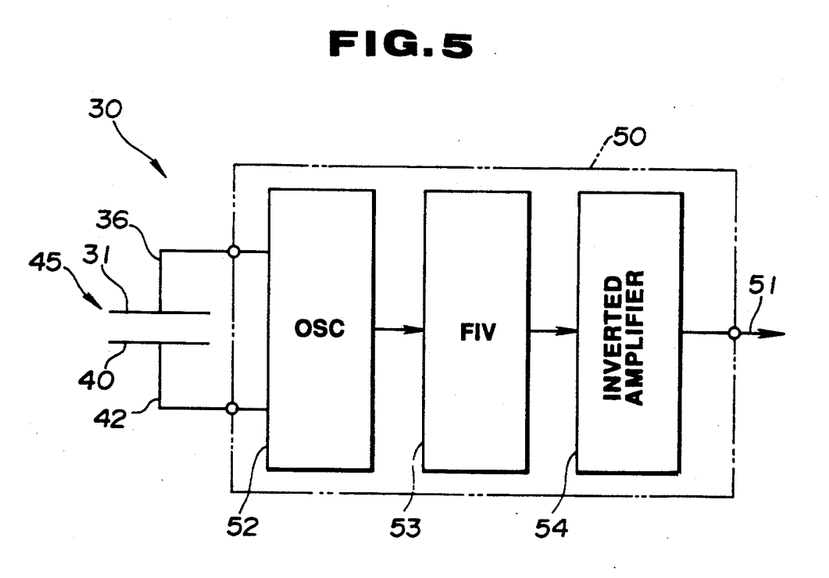
FIG. 5 is a schematic block diagram of the alcohol concentration measuring circuit used in the alcohol concentration sensor of FIG. 2.
Figure 6:
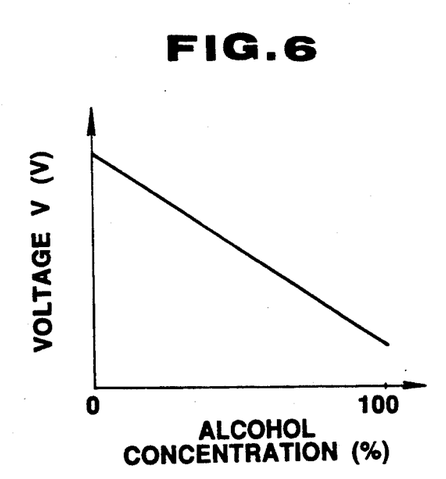
FIG. 6 is a graph of alcohol concentration versus voltage.
Figure 7:
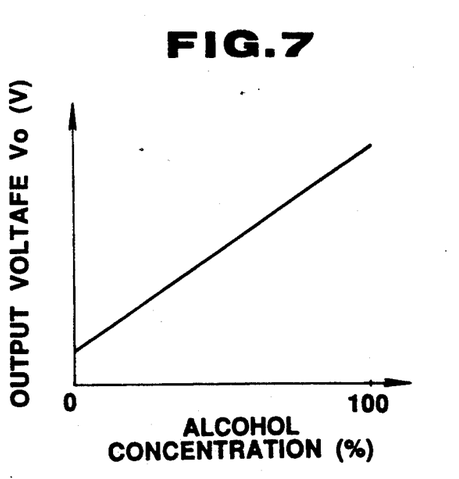
FIG. 7 is a graph of alcohol concentration versus output voltage.

Referring to FIG. 5, the alcohol concentration measuring unit 50 includes an LC oscillator (OSC) 52, a frequency-to-voltage converter (F/V) 53, and an inverted amplifier 54. The oscillator 52 is connected across the capacitive probe 45 comprised of the conductive tube member 31 and the conductive rod member 40 for producing a signal having a frequency f given as $$f = \frac{1}{2\pi \sqrt{L \times (Cs + Co)}}$$

where L is the inductance and Co is the electrostatic capacity of the capacitive probe placed in the atmosphere. The signal is fed from the oscillator 52 to the F/V converter 53 where its frequency f is converted into a corresponding voltage V. The voltage V has a linear relationship with the alcohol concentration M, as shown in FIG. 6. The voltage V is applied from the F/V converter 53 to the inverted amplifier 54 which inverts and amplifies the voltage V. The inverted and amplified voltage Vo is outputted from the inverted amplifier 54 through the line 51 to the engine control unit. The output voltage Vo has a linear relationship with the alcohol concentration M of the gasoline/alcohol fuel blend delivered to the fuel injector 20, as shown in FIG. 7. The engine control unit employs the output voltage Vo to calculate the correction factor ALK used in calculating the fuel delivery requirement.

Figure 8:
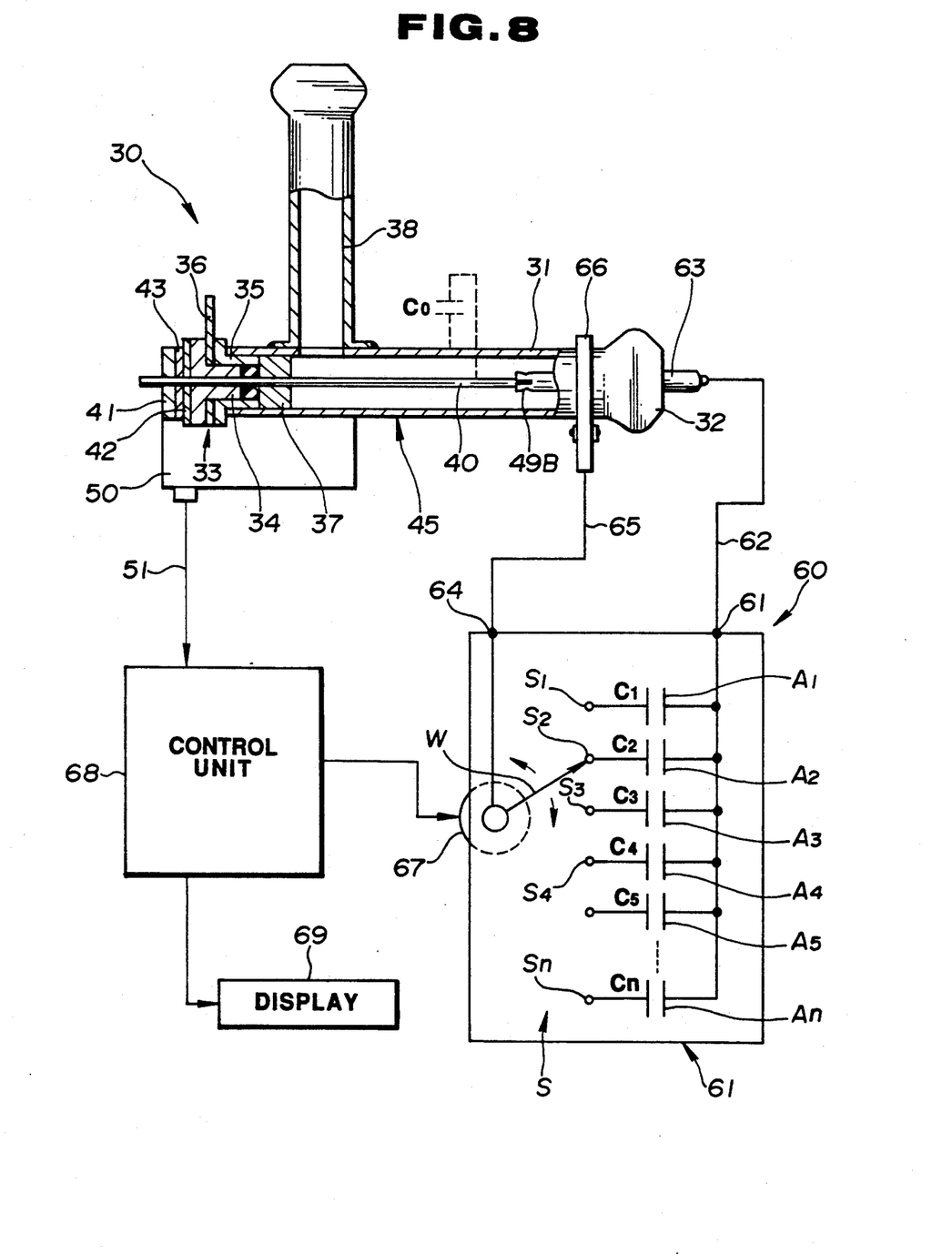
FIG. 8 is a schematic block diagram showing an alcohol concentration sensor testing apparatus made in accordance with the invention.

Referring to FIG. 8, there is shown an alcohol concentration sensor testing apparatus embodying the invention. The testing machine, generally designated by the numeral 60, is used to test an alcohol concentration sensor of the capacitive probe type as illustrated in FIG. 2. Like reference numerals have been applied to FIG. 8 with respect to the equivalent components shown in FIG. 2.

The testing machine 60 includes a capacitor circuit 61 comprised of a number of capacitors A1, A2, A3, ... An having different capacitances C1, C2, C3, ... Cn each corresponding to a predetermined alcohol concentration. One side of these capacitors is connected to a first terminal 61 which is connected through a line 62 to a first connector 63 for connection to the conducting rod member 40. The other side of the capacitors is connected to the switch contacts S1, S2, S3 ... Sn of a multi-position switch S having a wiper W connected to a second terminal 64 which is connected through a line 65 to a second connector 66 for connection to the conducting tube member 31. The second connector 66 may have a conductive metal strip fixed in contact around the conducting tube member 31. The multi-position switch S is operated, by means of a switch actuator 67, to connect the wiper W to a selected one of the switch contacts S1 to Sn so as to connect the corresponding one of the capacitors A1 to An in parallel with the capacitive probe 45 comprised of the conducting tube and rod members 31 and 40.

The testing apparatus 60 also includes a control unit 68 which may employ a digital computer. The control unit 68 has an input connected through the line 51 to the alcohol concentration measuring unit 50 and an output connected to a display unit 69. The control unit 68 reads the output voltage Vo from the inverted amplifier 54 (FIG. 5) and indicates the read value on the display unit 69. The control unit 68 may include a keyboard (not shown) operable to produce a command specifying a desired one of the capacitors A1 to An. The command is applied to the switch actuator 67 which thereby move the wiper W of the multi-position switch S into contact with the corresponding one of the switch contacts S1 to Sn. It is to be understood that the multi-position switch S may be operated manually. In this case, the switch actuator 67 is removed.

Figure 9:
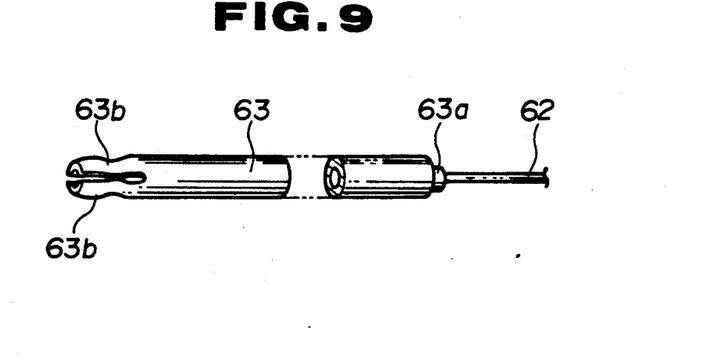
FIG. 9 is a perspective view in section showing the connector used in the alcohol concentration sensor testing apparatus of FIG. 8.

Referring to FIG. 9, the first connector 63 is taken in the form of a tubular member for receipt of the conducting rod member 40 therein. The tubular member has a rear end 63a connected to the line 62 and a split front end having two opposite tongues for providing resilient gripping engagement with the conducting rod member 40.

Figure 10:
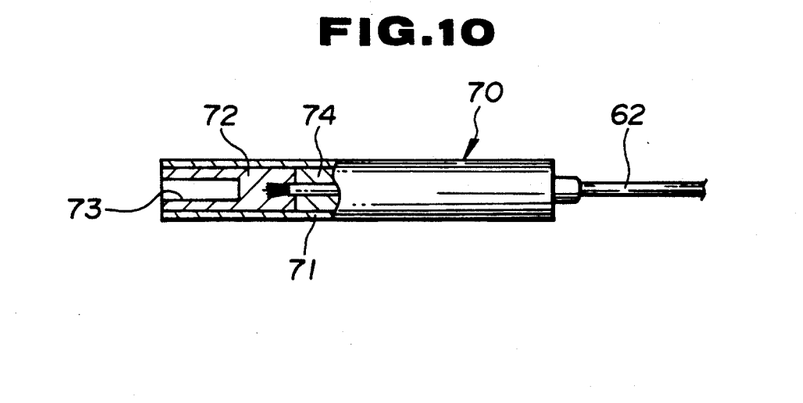
FIG. 10 is a side view in section showing a modified form of the connector.

Referring to FIG. 10, there is shown a modified form of the first connector. In this modification, the first connector 70 includes a tubular member 71 made of an insulating material having a small dielectric constant. This is effective to reduce the electrostatic capacity Co between the conducting tube and rod members 31 and 40. The tubular member 71 has a conducting end fitting 72 tightly fitted therein and formed with a center hole 73 for engagement with the conducting rod member 40. The end fitting 72 is made of a resilient material such as conductive resin for providing resilient gripping engagement with the conducting rod member 40. The end fitting is electrically connected to the line extending through an insulating member 74 charged in the tubular member 71.

Figure 11:
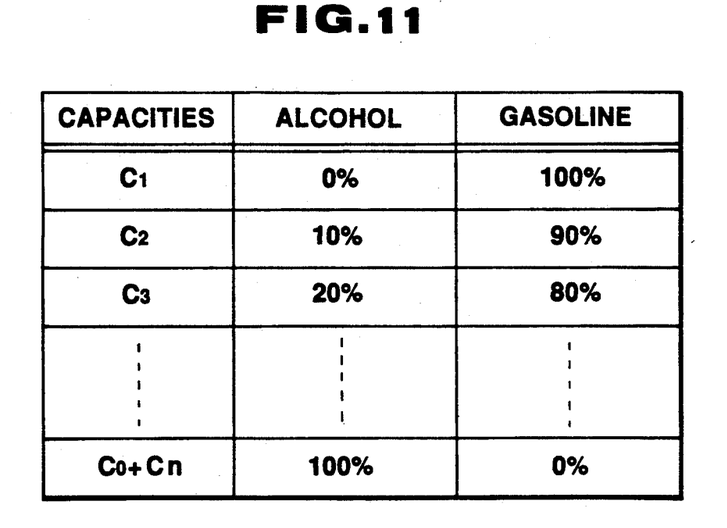
FIG. 11 is a table used in explaining the manner in which the capacities are selected.

Referring to FIG. 11, description is made to the manner in which the capacities C1, C2, ... Cn of the respective capacitors A1, A2, ... An are selected. It is now assumed that the capacitive probe 45 comprised of the conductive tube and rod members 31 and 40 has an electrostatic capacity Co when exposed to or placed in the atmosphere.

When the multi-position switch S is set to connect the wiper W to the switch contact S1, the capacitive probe 45 is connected in parallel with the capacitor A1 having a capacity C1. As a result, the voltage Vo applied through the line 51 to the control unit 68 corresponds to an electrostatic capacity Cs1 given as $$Cs1 = Co + C1$$

To use the capacitor A1 to simulate gasoline fuel contain no alcohol, its capacity C1 may be selected at a value equal to (Cs1−Co) where Cs1 is the electrostatic capacity of the conductive prove 45 exposed to gasoline fuel containing no alcohol concentration.

When the multi-position switch S is set to connect the wiper W to the switch contact S2, the capacitive probe 45 is connected in parallel with the capacitor A2 having a capacity C2. As a result, the voltage Vo applied through the line 51 to the control unit 68 corresponds to an electrostatic capacity CsZ given as $$Cs2 = Co + C2$$

To use the capacitor A2 to simulate gasoline/alcohol fuel blend containing 10% of alcohol, its capacity C2 may be selected at a value equal to (Cs2−Co) where Cs2 is the electrostatic capacity of the conductive prove 45 exposed to gasoline/alcohol fuel blend containing 10% of alcohol.

When the multi-position switch S is set to connect the wiper W to the switch contact S3, the capacitive probe 45 is connected in parallel with the capacitor A3 having a capacity C3. As a result, the voltage Vo applied through the line 51 to the control unit 68 corresponds to an electrostatic capacity Cs3 given as $$Cs3 = Co + C3$$

To use the capacitor A3 to simulate gasoline/alcohol fuel blend containing 20% of alcohol, its capacity C3 may be selected at a value equal to (Cs3−Co) where Cs3 is the electrostatic capacity of the conductive prove 45 exposed to gasoline/alcohol fuel blend containing 20% of alcohol.

When the multi-position switch S is set to connect the wiper W to the switch contact Si, the capacitive probe 45 is connected in parallel with the capacitor Ai having a capacity Ci. As a result, the voltage Vo applied through the line 51 to the control unit 68 corresponds to an electrostatic capacity Csi given as $$Csi = Co + Ci$$

To use the capacitor Ai to simulate gasoline/alcohol fuel blend having a predetermined alcohol concentration, its capacity Ci may be selected at a value equal to (Csi−Co) where Csi is the electrostatic capacity of the conductive prove 45 exposed to gasoline/alcohol fuel blend having the predetermined alcohol concentration.

When the multi-position switch S is set to connect the wiper W to the switch contact Sn, the capacitive probe 45 is connected in parallel with the capacitor An having a capacity Cn. As a result, the voltage Vo applied through the line 51 to the control unit 68 corresponds to an electrostatic capacity Csn given as $$Csn = Co + Cn$$

To use the capacitor An to simulate alcohol fuel containing no gasoline, its capacity Cn may be selected at a value equal to (Csn−Co) where Csn is the electrostatic capacity of the conductive prove 45 exposed to alcohol fuel containing no gasoline.

The operation of the alcohol concentration sensor testing apparatus of the invention is as follows:

First of all, the switch S is operated to connect the wiper W to the switch contact S1 so as to connect the capacitor A1 in parallel with the capacitive probe 45. The capacitor A1 has a capacity C1 selected as described in connection with FIG. 11, The control unit 68 reads the voltage Vo fed thereto from the alcohol concentration measuring unit 50. The read voltage value is indicated on the display unit 69. The indicated voltage value is compared with a value lying on the characteristic line as shown in FIG. 7 to determine whether the alcohol concentration sensor 30 is normal or defective. A similar operation is repeated successively for the capacitors A2 to An.

The control unit 68 may be arranged to store the read voltage value into a memory. The memory accumulates a number of voltage values read during the successive operations of the switch S. A determination is made whether the alcohol concentration sensor 30 is in order or defective by a comparison of the stored voltage values with the characteristic line as shown in FIG. 7. In this case, the control unit 68 may be arranged to produce commands to the switch actuator 67 so as to connect the capacitors A1 to An in a predetermined sequence to the capacitive probe 45. The control unit 68 reads a value of the output signal each time the capacitor connected to the capacitive probe is changed from one capacitor to another. The control unit 68 compares the read values with respective values specifying an output characteristic of a normal alcohol concentration sensor, as shown in FIG. 6 or 7.

It is to be understood that the inverted amplifier 54 may be removed. In this case, the read voltage values are compared with the characteristic line of FIG. 6 to determine whether or not the alcohol concentration sensor 30 is defective. Although the capacities C2, C3, ... are selected to simulate gasoline/alcohol fuel blend containing 10%, 20%, ... of alcohol, respectively, it is to be understood that they are not limited in any way to the values corresponding to 10%, 20%, ... of alcohol.

According to the invention, an alcohol concentration sensor can be tested simply by operating the multi-position switch S without troublesome operations of exposing the alcohol concentration sensor to gasoline/alcohol fuel blends having different alcohol concentrations. This is effective to increase the efficiency with which alcohol concentration sensors are tested to a remarkable extent.

What is claimed is:

1. An apparatus for testing an alcohol concentration sensor used in measuring an alcohol concentration of a fluid containing alcohol, the alcohol concentration sensor including a capacitive probe having a capacitance dependent upon the alcohol concentration of the fluid, and a circuit responsive to the capacitance of the capacitive probe for producing an output signal indicative of a sensed alcohol concentration, the apparatus comprising:

a plurality of capacitors having different capacitances each corresponding to a predetermined alcohol concentration;

first means for connecting a selected one of the capacitors in parallel with the capacitive probe;

second means for reading a value of the output signal when the selected capacitor is connected with the capacitive probe; and third means for comparing the read value with a value to be produced when the alcohol concentration sensor is exposed to an alcohol concentration predetermined for the selected capacitor to test the alcohol concentration sensor.

2. The apparatus as claimed in claim 1, wherein the second means includes a display for indicating the read value thereon.

3. The apparatus as claimed in claim 1, wherein the first means includes means for connecting the capacitors in parallel with the capacitive probe in a predetermined sequence.

4. The apparatus as claimed in claim 3, wherein the second means includes means for reading a value of the output signal each time the capacitor connected to the capacitive probe is changed from one capacitor to another.

5. The apparatus as claimed in claim 1, wherein the capacitive probe includes a conducting tube member for the fluid and a conducting rod member extending axially through the tube member.

6. The apparatus as claimed in claim 5, wherein the first means includes a conductive tube for resilient gripping engagement around the rod member, the conductive tube being covered with an insulating material having a small dielectric constant.

7. An apparatus for testing an alcohol concentration sensor used in measuring an alcohol concentration of a fluid containing alcohol, the alcohol concentration sensor including a capacitive probe having a capacitance dependent upon the alcohol concentration of the fluid, and a circuit responsive to the capacitance of the capacitive probe for producing an output signal indicative of a sensed alcohol concentration, the apparatus comprising:

a plurality of capacitors having different capacitances each corresponding to a predetermined alcohol concentration;

first means for connecting the capacitors in parallel with the capacitive probe in a predetermined sequence;

second means for reading a value of the output signal each time the capacitor connected to the capacitive probe is changed from one capacitor to another; and third means for comparing the read values with respective values specifying an output characteristic of a normal alcohol concentration sensor to test the alcohol concentration sensor.

8. The apparatus as claimed in claim 7, wherein the second means includes a display for indicating the read values thereon.

9. The apparatus as claimed in claim 7, wherein the capacity probe includes a conducting tube member for the fluid and a conducting rod member extending axially through the tube member.

10. The apparatus as claimed in claim 9, wherein the first means includes a conductive tube for resilient gripping engagement around the rod member, the conductive tube being covered with an insulating material having a small dielectric constant.

* * * * *